United States Patent [19]

Horriere et al.

[11] Patent Number: 4,698,334
[45] Date of Patent: Oct. 6, 1987

[54] FUNGICIDAL COMPOSITIONS BASED ON ALKYL PHOSPHITES

[75] Inventors: Daniel Horriere, Fontaines S/Saone; Maurice Chazalet, Anse, both of France

[73] Assignee: Rhone-Poulenc Agrochimie, Lyons, France

[21] Appl. No.: 357,567

[22] Filed: Mar. 12, 1982

Related U.S. Application Data

[63] Continuation-in-part of Ser. No. 133,143, Mar. 24, 1980, abandoned, which is a continuation of Ser. No. 869,234, Jan. 13, 1978, abandoned.

[30] Foreign Application Priority Data

Jan. 14, 1977 [FR] France ................. 77 01639

[51] Int. Cl.$^4$ ............ A01N 43/38; A01N 57/18; A01N 59/20
[52] U.S. Cl. ................. 514/141; 424/141; 424/143; 514/412; 514/417
[58] Field of Search .......... 424/223, 274; 514/141, 514/412, 417

[56] References Cited

U.S. PATENT DOCUMENTS 4,139,616 2/1979 Ducret et al. ................. 424/222

FOREIGN PATENT DOCUMENTS 1449394 9/1976 United Kingdom .

OTHER PUBLICATIONS

Chemical Week; Apr. 26, 1969, pp. 41+46.
ACTA Index Phytosanitaire, 1975, pp. 7, 185, 187, 191, 195–197 (English trans. of some page's).
Chemical Week; Apr. 12, 1969, pp. 50, 60+64.

Primary Examiner—Allen J. Robinson
Attorney, Agent, or Firm—Robert E. Burns; Emmanuel J. Lobato

[57] ABSTRACT

A fungicidal composition and method for the protection of vines against disease are provided. The composition which is applied to vines contains as active material a mixture of 1 part by weight of a monoester salt of a phosphorous acid of the formula

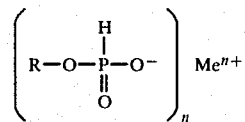

in which
R is an alkyl radical having 2 to 4 carbon atoms
Me is an alkali metal, alkaline earth, or aluminum atom
n is a whole number from 1 to 3 equal to the valence of Me
and from 0.05 to 8 parts of at least one contact fungicide selected from the group consisting of compounds having a base of copper, the metallic ethylene bisdithiocarbamates, and the derivatives of phthalimide.

19 Claims, No Drawings

FUNGICIDAL COMPOSITIONS BASED ON ALKYL PHOSPHITES

REFERENCE TO RELATED APPLICATIONS

This application is a continuation-in-part of copending application Ser. No. 133,143 filed Mar. 24, 1980, which is a continuation of application Ser. No. 869,234 filed Jan. 13, 1978 both abandoned.

BACKGROUND OF INVENTION

The present invention relates to fungicidal compositions having a base of metallic alkyl phosphites for the protection of vines, in particular against mildew, as well as a process for the antifungal treatment of vines by means of these compositions.

Fungicidal compositions based on alkyl phosphites which can be employed, in particular, for protecting vines from mildew have been proposed in U.S. Pat. No. 4,139,616 of Ducret et al. The active material of these compositions is described as having a systemic action, in contradistinction to previous antimildew fungicides; that is to say, the active material is carried from its point of application on the leaves to the other parts of the plant by the sap.

More thorough experimentation with these new fungicides on vines has shown that alkyl phosphites provide excellent protection of vine leaves against mildew, i.e. *Plasmopora viticola*, during the first months of vegetation, but that their fungicidal activity decreases substantially when the leaves become senescent. Thus, starting with the month of August, a progressive invasion is found by mildew on the old leaves, which are generally located at the base of the vine, while the rest of the foliage which has been more recently formed remains protected as a result of the systemic action of the alkyl phosphite based fungicide.

Certain conventional antimildew fungicides of the metallic ethylene-bis-dithiocarbamate type or derivatives of phthalimides exhibit good persistence on the vine but are not considered to have systemic activity.

SUMMARY OF THE INVENTION

An object of the present invention is a fungicidal composition which provides persistent protection for plants against fungal infection, especially mildew.

Another object of the present invention is a fungicidal composition which provides protection for plants, especially vine plants, against fungal infection that is more lasting than that provided by previous alkyl phosphite antifungal compositions.

A further object of the present invention is a method of treating plants to provide protection against mildew which lasts for an entire season.

Still a further object of the present invention is a composition for treating plants wherein the amount of an active agent used is less than that required in prior compositions to provide protection against fungal infection.

These and other objects are obtained by the invention disclosed below.

It has been found surprisingly, that excellent antimildew protection for the entire season is obtained when the vine is treated with mixtures of special alkyl phosphites and certain known antimildew agents having contact action, in which at least one of the active materials is present in an amount far less than that recommended when employed alone for the same use.

According to the invention, fungicidal compositions for the protection of vines, especially against mildew, contain as active material
a monoester of phosphorous acid of the formula

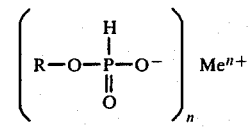

in which:
R is an alkyl radical containing from 2 to 4 carbon atoms,
Me is an alkali metal, alkaline earth metal, or aluminum atom, and
n is a whole number from 1 to 3, equal to the valence of Me, in combination with
a contact fungicide selected from
(a) fungicidal compositions having a base of copper such as copper oxychloride, copper sulfate neutralized with slaked lime and cuprous oxide,
(b) metallic ethylene bisdithiocarbamates, such as maneb (manganese ethylene bisdithiocarbamate), mancozeb (manganese-zinc ethylene bis-dithiocarbamate), and
(c) phthalimide type fungicides, such as captafol or N-(1,1,2,2-tetrachloroethylthio)-1,2,3,6-tetrahydrophthalimide and folpel, or folpet, or N-(trichloromethylthio)phthalimide, in which at least one of the active fungicidal materials is present in the mixture in an amount substantially less than that in which it is currently used by itself for the same purpose.

DESCRIPTION OF THE INVENTION

More precisely, the compositions of the invention which contain a mixture of at least one salt of a monoester of phosphorous acid of the above formula and at least one contact fungicide are effective antifungal agents when applied in an amount in which the individual constituents are present in amount of about 15% to 75% of the doses recommended for use when the constituents are applied by themselves. The relative proportions of each of the components of the composition of the invention are such that the mixtures have remarkable and unexpected synergistic characteristics.

Desirably, the instant compositions are applied by spraying and compositions useful for spraying including compositions containing an agriculturally acceptable carrier are included among the compositions of the invention.

Particularly significant and interesting results have been obtained in the case of mixtures containing 0.05 to 8 parts of contact fungicides to 1 part of alkyl phosphite. These mixtures, applied by leaf spraying, contain generally from 50 to 400 g.hl. of alkyl phosphite and from 20 to 400 g./hl. of contact fungicide.

Among the particularly preferred compositions are those which comprise calcium ethyl phosphite and a contact fungicide selected from folpel, copper oxychloride, Bordeaux mixture, mancozeb or captafol; the preferred ratios by weight of calcium ethyl phosphite to contact fungicide in such compositions are approximately 1:0.5, 1:0.8, 1:0.8, 1:0.6 and 1:0.33, respectively.

Also preferred are compositions comprising aluminum ethyl phosphite and folpel, preferably in a ratio by weight of about 1:0.5.

The above-mentioned compositions are useful for the treatment of vines against fungus infection, for example, mildew.

The following examples illustrate the synergistic behavior of the fungicidal mixtures in accordance with the invention, however, the examples are not to be construed as limiting the invention in any manner.

EXAMPLE 1

Several series of 10 vine stocks (Gamay variety) were subjected, from the spring until the beginning of August with watering in a very fine spray regularly, so as to cause a heavy contamination with mildew.

The vines were treated 8 times from May 12 to August 12 at intervals of 12 days on the average with a dispersion of wettable powders or solution of soluble powders of active materials consisting either of alkyl phosphites alone or of contact fungicides alone or else mixtures, formed just prior to use, of these two types of components. The spraying was effected by means of sprayers with deliveries of the order of 800 L/h.

The development of the attack of mildew on the foliage was checked and countings of the infested surface of the leaves were carried out regularly.

For each counting, the percentage contamination of the surface of the treated leaves is evaluated and referred to the percentage contamination of the surface of the control vines which were contaminated under the same conditions. This contamination ratio is then expressed in percent. The difference between the number obtained and 100 is then determined in order to express the percentage of protected surface.

The following results are given as of the end of September. This period is selected as being sufficiently late to be able to judge the intensity and persistence of the effectiveness close to the end of the season, at the time when the control vine are practically completely infested, but before the defoliation of the vines. It is, however, clear that under these conditions the surface of contaminated foliage corresponds substantially to that of the foliage treated.

The doses are expressed in grams of active material/hectoliter, those concerning the copper-base compounds being expressed as metallic copper.

The active materials appearing in the examples are the following:
copper oxychloride, applied as a wettable powder, 50% copper,
Bordeaux mixture having a base of copper sulfate with 20% copper, neutralized with slaked lime,
maneb: manganese ethylene bisdithiocarbamate, applied as a wettable powder with 80% active substance,
mancozeb: manganese-zinc ethylene bisdithiocarbamate (2.5%) as wettable powder with 8% active material,
captafol: N-(1,1,2,2-tetrachloroethylthio)-1,2,3,6-tetrahydrophthalimide, as wettable powder, 80% active material,
folpel or folpet: N-(trichloromethylthio)phthaliide, applied as wettable powder of 50% active material.

The synergism is evaluated on basis of these results by way of comparison between the protected surface Sm obtained with the mixture and the sum of the protected surfaces Sp and Sc obtained with the alkyl phosphite and the contact fungicide respectively, taken separately.

If the value Sm is greater than this sum, the effect is superior to what could be theoretically expected from the action of the mixture if the properties were simply additive; there is thus synergism.

Finally, in most cases, the action of the known fungicidal compound, used in its recommended dose, is indicated by way of memorandum at the top of each table. In order to make this synergism clearer, the sum Sp+Sc is indicated between parenthesis after the value Sm.

TABLE 1

MIXTURES WITH SODIUM ETHYL PHOSPHITE
Used As Soluble Powder With 80% Active Substance

| Sodium ethyl-phosphite g./hl. | Contact Fungicide g./hl. | % on September 26 of protected surface of leaves treated |
|---|---|---|
| 250 | copper oxychloride | Sp 4 |
| — | 80 | Sc 10 |
| 250 | 80 | Sm 60 (Sp + Sc = 14) |
| | maneb | |
| — | 280 (Recom. dose) for use | 54 |
| 250 | — | Sp 4 |
| — | 125 | Sc 36 |
| 250 | 125 | Sm 46 (Sp + Sc = 40) |
| | captafol | |
| — | 160 (Recom. dose) for use | 70 |
| 250 | — | Sp 4 |
| — | 50 | Sc 30 |
| 250 | 50 | Sm 55 (Sp + Sc = 34) |
| | folpel | |
| — | 150 (Recom. dose) for use | 54 |
| 250 | — | Sp 4 |
| — | 100 | Sc 25 |
| 250 | 100 | Sm 58 (Sp + Sc = 29) |

TABLE 2

MIXTURES HAVING A BASE OF ALUMINUM ETHYL PHOSPHITE
Used As Wettable Powder With 80% Active Material

| Aluminum ethyl-phosphite g./hl. | Contact Fungicide g./hl. | % on September 26 of protected surface of leaves treated |
|---|---|---|
| | copper oxychloride | |
| — | 500 (Recom. dose) for use | 90 |
| 250 | — | Sp 5 |
| — | 120 | Sp 12 |
| 250 | 120 | Sm 60 (Sp + Sc = 17) |
| | maneb | |
| — | 280 (Recom. dose) for use | 54 |
| 200 | — | Sp 4 |
| — | 200 | Sc 44 |
| 200 | 200 | Sm 56 (Sp + Sc = 48) |
| | captafol | |
| — | 160 (Recom. dose) for use | 70 |
| 250 | — | Sp 5 |
| — | 50 | Sc 30 |
| 250 | 50 | Sm 50 (Sp + Sc = 35) |
| | folpel | |
| — | 150 (Recom. dose) for use | 54 |
| 250 | — | Sp 5 |
| — | 100 | Sc 25 |
| 250 | 100 | Sm 56 (Sp + Sc = 30) |

Moreover, during the course of these tests, there could be noted the excellent activity of a mixture of aluminum ethyl phosphite and folpel against excoriosis (*Phomopsis viticola*), blockrot (*Guignardia bidwelli*), brenner (*Pseudopeziza tracheifila*) as well as the retarding action on oidium (*Uncinula necator*).

EXAMPLE 3

TABLE 3

MIXTURES HAVING A BASE OF MAGNESIUM ISOPROPYL PHOSPHITE
Used As A Soluble Powder With 50% Active Material

| Magnesium isopropyl phosphite g./hl. | Contact Fungicide g./hl. | % on September 26 of protected surface of leaves treated |
|---|---|---|
|  | copper oxychloride |  |
| — | 500 (Recom. dose) for use | 90 |
| 250 | — | Sp 4 |
| — | 120 | Sc 12 |
| 250 | 120 | Sm 50 (Sp + Sc = 16) |
|  | maneb |  |
| — | 280 (Recom. dose) for use | 54 |
| 200 | — | Sp 4 |
| — | 200 | Sc 44 |
| 200 | 200 | Sm 56 (Sp + SC = 48) |
| 250 | — | Sp 4 |
| — | 125 | Sp 36 |
| 250 | 125 | Sm 44 (Sp + Sc = 40) |
|  | captafol |  |
| — | 160 (Recom. dose) for use | 70 |
| 250 | — | Sp 4 |
| — | 50 | Sc 30 |
| 250 | 50 | Sm 60 (Sp + Sc = 34) |
|  | folpel |  |
| — | 150 | 54 |
| 250 | — | Sp 4 |
| — | 100 | Sc 25 |
| 250 | 100 | Sm 50 (Sp + Sc = 29) |

EXAMPLE 4

TABLE 4

MIXTURES HAVING A BASE OF CALCIUM ISOPROPYL PHOSPHITE
Used As Soluble Powder With 80% Active Material

| Calcium isopropyl phosphite g./hl. | Contact Fungicide g./hl. | % on September 26 of protected surface of leaves treated |
|---|---|---|
|  | maneb |  |
| — | 280 (Recom. dose) for use | 54 |
| 250 | — | Sp 4 |
| — | 125 | Sp 36 |
| 250 | 125 | Sm 46 (Sp + Sc = 40) |
|  | folpel |  |
| — | 150 | 54 |
| 250 | — | Sp 4 |
| — | 100 | Sc 25 |
| 250 | 100 | Sm 54 (Sp + Sc = 29) |

EXAMPLE 5

TABLE 5

MIXTURES WITH ALUMINUM ISOPROPYL PHOSPHITE
Used As Wettable Powder With 80% Active Material

| Aluminum isopropyl phosphite g./hl. | Contact Fungicide g./hl. | % on September 26 of protected surface leaves treated |
|---|---|---|
|  | copper oxychloride |  |
| — | 500 (Recom. dose) for use | 90 |
| 250 | — | Sp 4 |
| — | 120 | Sc 12 |
| 250 | 120 | Sm 50 (Sp + Sc = 16) |
|  | maneb |  |
| — | 280 (Recom. dose) for use | 54 |
| 200 | — | Sp 4 |
| — | 200 | Sc 34 |
| 200 | 200 | Sm 54 (Sp + Sc = 38) |
|  | captafol |  |
| — | 160 (Recom. dose) for use | 70 |
| 250 | — | Sp 4 |
| — | 50 | Sc 30 |
| 250 | 50 | Sm 50 (Sp + Sc = 34) |
|  | folpel |  |
| — | 150 (Recom. dose) for use | 54 |
| 250 | — | Sp 4 |
| — | 100 | Sc 25 |
| 250 | 100 | Sm 50 (Sp + Sc = 29) |

EXAMPLE 6

Tests under conditions of treatment very close to those described in Example 1 were carried out in another year with preformulated mixtures having a base of aluminum ethyl phosphite and mancozeb, each of the components being used in doses far less than the normal doses of use. The results, expressed as previously, are set forth in Table 6:

TABLE 6

MIXTURES WITH ALUMINUM ETHYL PHOSPHITE

| Aluminum ethylphosphite g./hl. | Contact Fungicide g./hl. | % on September 27 of protected surface referred to the surface treated |
|---|---|---|
|  | mancozeb |  |
| — | 280 (Recom. dose) for use | 85 |
| 150 | — | Sp 22 |
| — | 90 | Sc 64 |
| 150 | 90 | Sm 96 (Sp + Sc = 86) |
| 175 | — | Sp 25 |
| — | 100 | Sc 65 |
| 175 | 100 | Sm 96 (Sp + Sc = 90) |
|  | cupric oxychloride |  |
| — | 75 | Sp 34 |
| 150 | — | Sc 21 |
| 150 | 75 | Sm 79 (Sp + Sc = 55) |
| — | 100 | Sp 45 |
| 200 | — | Sc 32 |
| 200 | 100 | Sm 87 (Sp + Sc = 77) |
|  | Bordeaux mixture with 20% metallic copper |  |
| — | 75 | Sp 34 |
| 150 | — | Sc 21 |
| 150 | 75 | Sm 93 (Sp + Sc = 55) |
|  | cuprous oxide |  |
| — | 75 | Sp 34 |
| 150 | — | Sc 21 |
| 150 | 75 | Sm 87 (Sp + Sc = 55) |

Excellent protection of the vine up to the end of the season was obtained by applying to it, either in pre-prepared mixture or in mixture formed on the spot, compositions having a base of the above mixtures associated with another contact fungicide. This applies in particular to compositions containing:
from 80 to 150/g./hl. of aluminum ethyl phosphite from 40 to 60 g./hl. of folpel
from 60 to 80 g./hl. of mancozeb
from 130 to 240 g./hl. of copper.

Similar results are obtained when the alkyl phosphites tested are replaced in the mixtures by the following compounds:
magnesium ethyl phosphite
magnesium isobutyl phosphite
magnesium sec.butyl phosphite
calcium isobutyl phosphite
aluminum N-butyl phosphite
aluminum sec.butyl phosphite
aluminum isobutyl phosphite.

EXAMPLE 7

Several series of 10 vine-stocks (Gamay variety) were subjected from spring to the start of August, to regular watering by very fine spray, so as to cause severe combination with mildew (*Plasmopora viticola*).

The vine-stocks were treated 9 times, from May 30th to August 22nd at average intervals of 11 days, with dispersions of wettable powders or solutions of soluble powders of active materials consisting either solely of calcium ethyl phosphite or solely of contact fungicides or of mixtures, prepared just before use, of these two types of constituents. Spraying was carried out by means of sprayers delivering of the order of 800 l/hectare. The development of the mildew attack on the foliage was observed and counts of the invaded surface of the leaves were made regularly.

For each count are estimated over the total surface of the leaves, the percentage of contamination of the surface of the treated leaves Sx and that of the surface of the control vinestocks $S_T$, the latter having been contaminated under the same conditions. Thereafter, a coefficient of efficacy is calculated using the formula $S_T - Sx/ST$. The results given in the Tables 7 and 8 are given for a count at the beginning of October.

This period is selected as being sufficiently late to be able to judge the intensity and persistence of the effectiveness of the various treatments close to the end of the season, at a time when the controls are practically completely infested, but before the defoliation of the vines.

The doses are expressed in g. of active material/hl., those relating to the compounds based on copper being expressed in terms of copper metal.

The active materials (a.m.) used are the following: calcium ethyl phosphite as a wettable powder having the following composition by weight:

| | |
|---|---|
| calcium ethyl phosphite | 80% |
| calcium lignosulphate | 4% |
| sodium isopropylnaphthalene sulphonate | 4% |
| kaolin | 12% | folpet: N-(trichloromethylthio)phthalimide as a wettable powder containing 50% by weight of active material
copper oxychloride as a wettable powder containing 50% by weight of copper
Bordeaux mixture based on copper sulphate neutralized with calcium hydroxide, and containing 20% by weight of copper.

The synergism is evaluated on the basis of these results by comparison between the coefficient of efficacy Sm obtained with the mixture and the sum of the coefficients of efficacy Sp and Sc obtained with the ethylphosphite and the contact fungicide used separately.

If the value Sm is greater than the sum, Sp+Sc, the effect is superior to what could be theoretically expected from the action of the mixture if the properties of the components were simply additive; there is thus synergism. In order to make this synergism clearer, the sum Sp+Sc is indicated between parenthesis after the value Sm.

TABLE 7

MIXTURES WITH CALCIUM ETHYL PHOSPHITE

| Calcium ethyl phosphite g.a.m. | Contact fungicide g.a.m. | Coefficient of efficacy on 3rd October |
|---|---|---|
| | folpel | |
| 150 | — | Sp 18 |
| — | 75 | Sc 37 |
| 150 | 75 | Sm 86 (Sp + Sc = 55) |
| | copper oxychloride | |
| 150 | — | Sp 18 |
| — | 120 | Sc 43 |
| 150 | 120 | Sm 71 (Sp + Sc = 61) |
| | Bordeaux mixture | |
| 150 | — | Sp 18 |
| — | 120 | Sc 41 |
| 150 | 120 | Sm 72 (Sp + Sc = 59) |

EXAMPLE 8

Another year a field trial is carried out using the same procedure as that described in Example 7, with the following particular conditions:
the vine-stocks are treated 8 times from May 31 up to August 9, at an average interval of 10 days:
the active materials tested are as follows:

| | |
|---|---|
| calcium ethyl phosphite | 80% |
| calcium lignosulphate | 4% |
| sodium isopropylnaphthalene sulphonate | 4% |
| kaolin | 12% | mancozeb: manganese and zinc (2.5% w/w) ethylenebisdithiocarbamate as a wettable powder containing 80% w/w of active ingredient captafol: N-(1,1,2,2-tetrachloroethylthio)-1,2,3,6-tetrahydrophthalimide as a suspension concentrate containing 480 g./l. of active material.

The results are expressed in Table 8 in the same way as in Example 7.

TABLE 8

MIXTURES WITH CALCIUM ETHYL PHOSPHITE

| Calcium ethyl phosphite | Contact fungicide g.a.m./hl. | Coefficient of efficacy on October 1 |
|---|---|---|
| | mancozeb | |
| 150 | — | Sp 9 |
| — | 90 | Sc 58 |
| 150 | 90 | Sm 83 (Sp + Sc = 67) |
| | captafol | |
| 150 | — | Sp 9 |
| — | 50 | Sc 62 |
| 150 | 50 | Sm 86 (Sp + Sc = 71) |

EXAMPLE 9

The test described below illustrates the synergistic behavior of a fungicidal composition according to the invention comprising aluminum ethyl phosphite and folpel in a ratio of 1:0.5 by weight.

Several series of 10 vine-stocks (Gamay variety) were subjected, from spring to the start of August, to regular watering by very fine spray, so as to cause severe contamination with mildew (*Plasmopara viticola*).

The vine-stocks were treated 8 times from May 31 to August 9, at average intervals of 10 days, with dispersions of wettable powders or solutions of soluble powders of active materials consisting either solely of alkyl phosphite or solely of contact fungicide or of a mixture, prepared just before use, of these two constituents. Spraying was carried out by means of sprayers delivering of the order of 800 l/hectare. The development of the mildew attack was observed and counts of the invaded surface were made regularly.

For each count are estimated over the total surface of the leaves the percentage of contamination of the surface of the treated leaves Sx and that of the surface of the control vine-stocks $S_T$, the latter having been contaminated under the same conditions. Thereafter a coefficient of efficacy is calculated using the formula $S_T - Sx/S_T$. The results in Table 9 given for a count at the end of September.

This period is selected as being sufficiently late to be able to judge the intensity and persistence of the effectiveness of the various treatments close to the end of the season, at a time when the controls are practically completely infested, but before the defoliation of the vines.

The doses are expressed in grams of active material/hectoliter. The contact fungicide appearing in the Test is folpel or folpet, i.e. N-(trichloromethylthio)phthalimide, applied as a wettable powder containing 50% w/w active material.

The synergistic effect is evaluated on the basis of these results by comparison of the coefficient of efficacy Sm obtained with the mixture and the sum of the coefficients of efficacy Sp and Sc obtained with the alkyl phosphite and the contact fungicide respectively, taken separately.

If the value Sm is greater than this sum, the effect is superior to what could theoretically be expected from the action of the mixture if the properties were simply additive; there is thus synergism. In order to make this synergism clearer, the sum Sp+Sc is indicated in parenthesis after the value Sm.

TABLE 9

| MIXTURES BASED ON ALUMINUM ETHYL PHOSPHITE | | | |
|---|---|---|---|
| Ratio contact fungicide/alkyl phosphite | Aluminum ethyl-phosphite g./hl. | Folpel g./hl. | Coefficient of efficacy on 26th September |
| 0.5/1 | 200 | — | Sp 4 |
|  | — | 100 | Sc 25 |
|  | 200 | 100 | Sm 56 (Sp + Sc = 29) |

All these examples clearly show that:

On the one hand, the protective action of the alkyl phosphites alone on the aged leaves, that is to say the treated foliage, is insufficient due to a lack of permanence. These compounds therefore cannot be used by themselves to assure protection of the treated foliage up to the end of the season.

On the other hand, the contact fungicides in their recommended dose assure a certain amount of protection which may be excellent, as in the case of the copper-base compounds. However, as soon as the doses are substantially decreased, the action of the products, still considered residual, becomes very greatly reduced, to the point of making them ineffective in these doses.

Knowing thus that the alkyl phosphites assure good protection at the start of the season and the contact fungicides good protection for the rest of the season, one could have expected an action which was merely complementary in time. It is completely surprising that at the end of the season, the protection of foliage treated with compositions of the invention has been found to be not only superior to that of the contact fungicides used by themselves, but far superior to the theoretical sum of the protections which are obtained with each of the components taken individually in the same doses as in the mixture.

The synergism noted is observed for a given selection of alkyl phosphites with certain contact fungicides, preferably with compounds having a base of copper, mancozeb and folpel.

The fungicidal compositions in accordance with the invention, contain as active material, a mixture comprising from 0.05 to 8 and preferably from 0.1 to 2 parts by weight of contact fungicides per part of alkyl phosphite. The compositions are applied preferably by leaf spraying in an amount of 50 to 400 g./hl. of contact fungicide.

More precisely, the copper base mixtures contain 0.15 to 2 parts of metallic copper per part of alkyl phosphite.

The mixtures having a base of metallic ethylene bisdithiocarbamate contain from 0.2 to 2 parts of these fungicides per part of alkyl phosphite.

The mixtures having a base of phthalimide derivatives contain from 0.1 to 1.2 parts of these fungicides per part of alkyl phosphite.

The ternary mixtures, that is to say, mixtures containing two contact fungicides, contain by weight preferably from 0.25 to 0.75 part of phthalimide derivatives or 0.4 to 1 part of metal ethylene bisdithiocarbamate and 0.85 to 3 parts of metallic copper per part of ethyl phosphite.

For their use in practice, the mixtures in accordance with the invention are rarely used alone. Generally, they are part of formulations which, in most cases, include in addition to the active material of the invention, also a carrier or support and/or a surface-active agent.

The expression "carrier" or "support" within the meaning of the present specification refers to an organic or inorganic material, natural or synthetic, with which the active material is associated to facilitate its application to the plant, the seeds, or the soil, or its transportation or handling. The support may be solid (clays, natural or synthetic silicates, resins, waxes, solid fertilizers) or liquid (water, alcohols, ketones, petroleum fractions, chlorinated hydrocarbons, liquified gases).

The surface-active agent may be an emulsifying, dispersing, or wetting agent, whether ionic or nonionic. Mention may be made, by way of example of salts of polyacrylic acids, lignin-sulfonic acids, ethylene oxide condensates with fatty alcohols, fatty acids, or fatty amines.

The compositions in accordance with the invention can be prepared in the form of wettable powders, soluble powders, solutions, emulsifiable concentrates, emulsions, concentrates in suspension, and suspensions.

The wettable powders are customarily prepared in such a manner that they contain from 20 to 95% by weight of material and they customarily contain, in addition to a solid support, from 0 to 5% by weight of wetting agent, from 3 to 10% by weight of a dispersing agent, and, when necessary, from 0 to 10% by weight of one or more stabilizers and/or other additives, such as penetration agents, adhesives, or anti-clodding agents, coloring substances, etc. By way of example the composition of a wettable powder is given herewith:

| | |
|---|---|
| active material | 50% |
| calcium lignosulfonate (deflocculant) | 5% |
| anionic wetting agent (alkaline alkyl naphthalene sulfonate) | 1% |
| anticlodding silica | 5% |
| kaolin (filler) | 39% |

The water soluble powders are obtained by mixing 20 to 95% by weight of active material, 0 to 10% of an anticlodding filler and 0 to 1% of a wetting agent, the balance consisting of a water-soluble filler, primarily a salt.

An example of the composition of a water soluble powder follows:

| | |
|---|---|
| active material | 80% |
| anionic wetting agent (alkaline alkyl naphthalene sulfonate) | 0.5% |
| anticlodding silica | 4% |
| sodium sulfate (soluble filler) | 15.5% |

Aqueous dispersions and emulsions, for instance the compositions obtained by diluting with water a wettable powder or an emulsifiable concentrate in accordance with the invention, are included within the general scope of the present invention. These emulsions may be of the water-in-oil type or of the oil-in-water type and they may have a thick consistency like that of mayonnaise.

What we desire to claim and protect by Letters Patent is:

1. A fungicidal composition for the protection of vines against fungus diseases, which comprises as the active material a mixture of:

1 part by weight of a monoester salt of a phosphorous acid of the formula

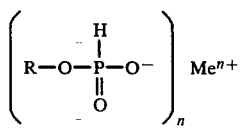

in which

R is an alkyl radical having 2 to 4 carbon atoms,

Me is an alkali metal, alkaline earth, or aluminum atom and n is a whole number from 1 to 3 equal to the valence of Me and from about 0.2 to 0.5 parts of at least one phthalimide contact fungicide selected from the group consisting of N-(1,1,2,2-tetrachloroethylthio)-1,2,3,6-tetrahydrophthalimide and N-(trichloromethylthio)-phthalimide.

2. A composition according to claim 1 in which said contact fungicide is N-(trichloromethylthio)-phthalimide.

3. A composition according to claim 1 or 2 in which the alkyl phosphite is an ethyl phosphite.

4. A composition according to claim 1 or 2 in which the alkyl phosphite is a propyl phosphite.

5. A composition according to claim 1 or 2 in which the alkyl phosphite is an isopropyl phosphite.

6. A composition according to claim 1 or 2 in which the alkyl phosphite is a butyl phosphite.

7. A composition according to claim 1 in which the monoester salt of phosporous acid is aluminum ethyl phosphite and the contact fungicide is N-(trichloromethylthio)phthalimide.

8. A composition according to claim 7 in which the monoester salt of phosphorous acid is aluminum ethyl phosphite and the contact fungicide is N-(trichloromethylthio)phthalimide.

9. The composition of claim 1 which comprises aluminum ethyl phosphite and the contact fungicide N-(trichloromethylthio)phthalimide in a ratio by weight of said phosphite to said contact fungicide of about 1:0.5.

10. The composition according to claim 1 wherein the alkyl radical of said monoester salt of phosphorous acid contains 2 to 3 carbon atoms.

11. The composition according to claim 10 wherein the contact fungicide is N-(trichloromethylthio)phthalimide and is present in an amount of about 0.4 to 0.5 parts per part by weight of said monoester salt of phosphorous acid.

12. A fungicidal composition for the protection of vines against fungus diseases, which comprises as the active material a mixture of:

1 part by weight of a monoester salt of a phosphorous acid of the formula

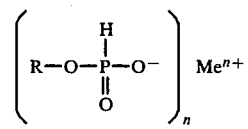

in which

R is an alkyl radial having 2 to 4 carbon atoms,

Me is an alkali metal, alkaline earth, or aluminum atom and n is a whole number from 1 to 3 equal to the valence of Me, and from about 0.2 to 0.4 parts of at least one phthalimide contact fungicide selected from the group consisting of N-(1,1,2,2-tetrachloroethylthio)-1,2,3,6-tetrahydrophthalimide and N-(trichloromethylthio)-phthalimide.

13. A composition according to claim 12 in which said contact fungicide is N-(trichloromethylthio)-phthalimide.

14. A composition according to claims 1, 2 or 10 in which Me is a cation selected from the group consisting of sodium, calcium, magnesium, and aluminum.

15. A composition according to claims 1, 2 or 10 in which said phosphite is aluminum or calcium ethyl phosphite.

16. A composition according to claim 10 or 12 which contains both of said contact fungicides.

17. A process for treating vines to protect said vines from fungal infection which comprises applying a composition defined in claims 1, 2 or 10 to said vines in an amount effective to control said fungal infection.

18. The process of claim 17 wherein the alkyl phosphite and contact fungicide are present in said composition in an amount such that about 50 to 400 g./hl. of alkyl phosphite and 20–400 g./hl. of the contact fungicide are applied to said vines.

19. The process of claim 17 wherein the fungal infection is mildew.

* * * * *